United States Patent [19]

Melvin, Jr

[11] 4,360,700

[45] Nov. 23, 1982

[54] INTERMEDIATES FOR MAKING 1-(3-BENZYLOXYPHENYL)-1,1-DIMETHYL-HEPTANE

[75] Inventor: Lawrence S. Melvin, Jr, Ledyard, Conn.

[73] Assignee: Pfizer Inc., New York, N.Y.

[21] Appl. No.: 317,223

[22] Filed: Nov. 2, 1981

[51] Int. Cl.³ .................. C07C 43/225; C07C 43/23
[52] U.S. Cl. .................................. 568/644; 568/647; 568/631
[58] Field of Search ....................... 568/644, 647, 631

[56] References Cited

U.S. PATENT DOCUMENTS 4,284,829 8/1981 Althuis et al. ...................... 568/764
4,285,867 8/1981 Johnson et al. .................. 568/734 X

OTHER PUBLICATIONS

Miller, Jour. Org. Chem., vol. 31 (1966) 908–912.
Kennedy, Jour. Org. Chem., vol. 35 (1970) 532–535.
Weygand/Hilgetag, Preparative Org. Chem. (1972) 214–219.

*Primary Examiner*—Bernard Helfin
*Attorney, Agent, or Firm*—Charles J. Knuth; Albert E. Frost; Peter C. Richardson

[57] ABSTRACT

Process for making 1-(3-benzyloxyphenyl)-1,1-dimethylheptane, a valuable intermediate for the preparation of analgesic agents, which comprises benzylation of 3-hydroxyacetophenone to produce 3-benzyloxyacetophenone which is converted to 1-(3-benzyloxyphenyl)-1-methylheptan-1-ol via Grignard reaction with n-hexylmagnesium bromide; chlorination of said heptanol by reaction with hydrogen chloride followed by methylation of the thus-produced 1-(3-benzyloxyphenyl)-1-chloro-1-methylheptane with trimethylaluminum.

2 Claims, No Drawings

INTERMEDIATES FOR MAKING 1-(3-BENZYLOXYPHENYL)-1,1-DIMETHYLHEPTANE

BACKGROUND OF THE INVENTION

1. Field of the Invention

This invention relates to a novel and efficient process for making 1-(3-benzyloxyphenyl)-1,1-dimethylheptane, a valuable intermediate for syntheses of 2-(cyclic- and acyclic-substituted)-5-(1,1-dimethylheptyl)phenols useful as analgesic agents as is described in U.S. Pat. Nos. 4,285,867 and 4,284,829, issued Aug. 25, 1981 and Aug. 18, 1981, respectively. More specifically it comprises methylation of 1-(3-benzyloxyphenyl)-1-chloro-1-methylheptane by means of trimethylaluminum. Said chloroheptane reactant is prepared by chlorination with hydrogen chloride of 1-(3-benzyloxyphenyl)-1-methylheptan-1-ol, itself prepared by reaction of n-hexylmagnesium bromide with 3-benzyloxyphenylacetophenone which in turn is prepared by benzylation of 3-hydroxyacetophenone.

2. Description of the Prior Art

The reaction of trialkylaluminums with chlorohydrocarbons is reported by Miller in J. Org. Chem. 31, 908–912 (1966), by Kennedy, J. Org. Chem. 35, 532 (1970), and by references cited therein. Miller notes that of the reactions of halohydrocarbons with alkylaluminums, the preparation of alkylbenzenes by alkylation to (alpha- and beta-haloalkyl)benzenes is the most promising from a synthetic standpoint.

Until the present invention, 1-(3-benzyloxyphenyl)-1,1-dimethylheptane was prepared from methyl 3-hydroxybenzoate as described in U.S. Pat. No. 4,285,867, issued Aug. 25, 1981. The overall sequence comprised benzylation of the phenolic group to produce methyl 3-benzyloxybenzoate followed by reaction of said ether ester with methyl magnesium iodide to give 3-benzyloxybenzene-2-propanol. Reaction of the thus-produced propanol derivative with hydrochloric acid afforded 2-(3-benzyloxyphenyl)-2-chloropropane which was then reacted with n-hexylmagnesium bromide to provide 1-(3-benzyloxyphenyl)-1,1-dimethylheptane.

SUMMARY OF THE INVENTION

It has now been found that 1-(3-benzyloxyphenyl)-1,1-dimethylheptane can be readily prepared in much higher yields than afforded by the previously known synthesis. The process, a multistep process, comprises benzylation of 3-hydroxyacetophenone followed by reaction of the benzyl ether with n-hexylmagnesium bromide to produce 1-(3-benzyloxyphenyl)-1-methylheptan-1-ol. The alcohol is then treated with hydrogen chloride to afford the corresponding chloro compound which is then methylated by reaction with trimethyl aluminum to give 1-(3-benzyloxyphenyl)-1,1-dimethylheptane. The product thus obtained is more easily purified than is the product produced by the prior art process.

DETAILED DESCRIPTION OF THE INVENTION

The overall process described and exemplified herein for making 1-(3-benzyloxyphenyl)-1,1-dimethylheptane comprises, as first step, benzylation of 3-hydroxyacetophenone. The reaction is carried out by reacting 3-hydroxyacetophenone and benzyl chloride or benzyl bromide in a reaction-inert solvent at a temperature of from about 50° C. to the reflux temperature of the solvent in the presence of an acid acceptor. In general, the 3-hydroxyacetophenone and benzyl chloride, or bromide, are reacted in equimolar or approximately equimolar proportions; i.e., from 1:1 to 0.9:1. From an economical standpoint a slight excess of benzylchloride or bromide is used to ensure greater utilization of the more expensive 3-hydroxyacetophenone reactant. The acid acceptor is used in equimolar amount based upon the amount of benzylchloride or bromide used. Suitable acid acceptors are alkali metal carbonates, alkaline earth metal carbonates and anion exchange resins such as those consisting of polystyrene beads having —N(C$_2$H$_5$)$_2$ groups attached to the polymers.

Suitable solvents for the reactions are acetone, methylethyl ketone, tetrahydrofuran, benzene, toluene and dioxane.

The benzyl ether is separated from the reaction mixture by standard procedures and purified by vacuum distillation.

The function of the benzyl group is to protect the phenolic hydroxy group. Suitable protective groups are those which do not interfere with subsequent reactions of said 3-(protected hydroxy) acetophenone and which are easily removable to regenerate the hydroxy group. Representative protective groups, in addition to benzyl, are methyl, ethyl and substituted benzyl wherein the substituent is, for example, alkyl having from 1 to 4 carbon atoms, halo (Cl, Br, F, I), and alkoxy having from one to four carbon atoms.

The exact chemical structure of the protecting group is not critical to this invention since its importance resides in its ability to perform in the manner described above.

The selection and identification of appropriate protecting groups can easily and reaily be made by one skilled in the art. The suitability and effectiveness of a group as a hydroxy protecting group are determined by employing such a group in the above-illustrated reaction sequence. It should, therefore, be a group which is easily removed to permit restoration of the hydroxy group. The benzyl group, a favored protecting group, is removed by catalytic hydrogenolysis or acid hydrolysis.

The next step of the overall process comprises extension of the acetyl side chain to the desired length and simultaneous conversion of the keto group of said side chain to hydroxy. This is conveniently accomplished by the Grignard reaction with 1-n-hexyl-magnesium bromide in a reaction-inert solvent at a temperature of from about −10° C. to 50° C. Suitable solvents are tetrahydrofuran, dioxane or diethylether. An excess, generally up to 5% excess, of magnesium is used to ensure more complete utilization of the n-hexylbromide reactant. The Grignard reagent and acetophenone derivative are reacted in approximately equimolar proportions; i.e., from about 1.0:1.0 to about 1.10 to 1.0. The reaction mixture is then hydrolyzed by treatment with water to generate the alcohol.

The thus-produced 1-(3-benzyloxyphenyl)-1-methylheptan-1-ol is then converted by reaction with excess aqueous hydrogen chloride to the corresponding 1-(3-benzyloxyphenyl)-1-chloro-1-methylheptane. The tertiary alcohol group is smoothly replaced by a chloro atom simply by agitating it with excess aqueous hydrochloric acid at ambient temperature. Molar ratios of up to 10 moles of HCl per mole of hydroxy derivative are especially useful. Higher ratios can be used but offer no advantage. Temperatures above or below ambient temperature are operative but are generally avoided to eliminate the need for heating or cooling of the reaction mixture. Alternatively, the hydroxy group can be replaced by bromo or iodo by substituting hydrogen bromide or hydrogen iodide for hydrogen chloride. However, aqueous hydrochloric acid is favored over the use of other halogenating agents for reasons of simplicity and economy. The chloro derivative is recovered by extraction with a water immiscible solvent.

The chloro derivative is then methylated by reaction with trimethylaluminum in a reaction-inert solvent. Representative solvents for the reaction are dichloromethane, hexane, xylene, toluene, diethylether, cyclopentane and methylchloride. The reaction is conducted at from about −50° C. to 10° C. for periods of from about 15–25 hours. The chloro derivative and trimethylaluminum are reacted in molar porportions of from 1:1 to 1:3. The methylated product is recovered by cautious hydrolysis of the reaction mixture, for example, by adding it to ice with simultaneous addition of concentrated hydrochloric acid. The product is isolated by separating the organic phase from the hydrolysis mixture and removal of the organic solvent therefrom.

The 1-(3-benzyloxyphenyl)-1,1-dimethylheptane thus prepared is a valuable intermediate, especially for the synthesis of analgesics. It is converted by bromination with bromine according to known technology to 1-(3-benzyloxy-4-bromophenyl)-1,1-dimethylheptane, also known as (2-benzyloxy-1-bromo-4-(1,1-dimethylheptyl)benzene.

EXAMPLE 1

3-Benzyloxyacetophenone

A mechanically stirred mixture of 1 kg. (7.35 mole) of 3-hydroxyacetophenone, 1.035 kg. (7.5 mole) anhydrous potassium carbonate and 0.945 kg. (7.5 mole) of benzylchloride in 4.1 of acetone was heated at reflux for 24 hours after which 0.1035 kg. (0.75 mole) portion of potassium carbonate and 0.0945 kg. (0.75 mole) portion of benzylchloride were added and refluxing continued. This addition was repeated after 72 hours of refluxing and refluxing continued for 96 hours. The reaction was cooled, filtered and the filtrate concentrated on a rotovapor. The filtrate was then treated with 0.202 kg. (2.0 mole) triethylamine and stirred overnight. The reaction was diluted with 1 liter ether and filtered. The filtrate was evaporated and the residue distilled to yield 1.429 kg. (86%) of the title compound as an oil.

BP 160° C. (0.3 torr).

IR (CHCl$_3$) 1695, 1605, 1595, 1493 and 1433 cm$^{-1}$.

PMR (CDCl$_3$) $\delta$2.52 (s, CH$_3$), 5.03 (s, CH$_2$) and 7.0–7.7 (m, Ph).

EXAMPLE 2

1-(3-Benzyloxyphenyl)-1-methylheptan-1-ol

To a slurry of 186 g. (7.65 mole) of magnesium in 3.5 l. of tetrahydrofuran was added 1.023 l. (7.29 mole) of 1-bromohexane over 2 hours. The resultant Grignard solution was allowed to cool to 25° C. A solution of 1.098 kg. (4.86 mole) of 3-benzyloxyacetophenone in 1 liter of tetrahydrofuran was added to the Grignard solution over a 3 hour period. The reaction temperature was maintained at 12°–18° C. with an ice bath. Upon completion of the addition the reaction was allowed to stir overnight at 25° C. A solution of 61.5 g. (3.42 mole) of water in 120 ml. tetrahydrofuran was added to the reaction over 15 minutes and, after stirring 20 minutes longer 0.440 l. (1.1 mole) of 2.5 M hexylmagnesium bromide in ether, was added. The reaction was stirred 20 hours longer and then quenched by slow addition to a mixture of 6 l. water and ice and 750 g. (14.2 mole) of ammonium chloride. The organic extract was removed and the aqueous extract was extracted with 1 liter of ether. The combined organic extract was washed with 1 liter of saturated sodium chloride, dried over magnesium sulfate and evaporated to yield 1.424 kg. (94%) of the title compound as an oil.

PMR (CDCl$_3$) $\delta$0.83 (m, CH$_3$), 1.20 (m, CH$_2$), 1.51 (s, CH$_3$), 1.72 (s, OH), 1.8 (m, CH$_2$), 5.02 (s, CH$_2$) and 6.7–7.6 (m, PhH).

EXAMPLE 3

1-(3-Benzyloxyphenyl)-1,1-dimethylheptane

A mixture of 660 g. (2.11 mole) of 1-(3-benzyloxyphenyl)-1-methylheptan-1-ol and 1.70 l. of concentrated hydrochloric acid was vigorously stirred for 40 minutes. The reaction was diluted with 600 ml. of hexane and the layers separated. The organic extract was washed with 500 ml. saturated sodium bicarbonate, 500 ml. saturated sodium chloride, dried over magnesium sulfate and evaporated to yield 664 g. (2.0 M) of intermediate 1-(3-benzyloxyphenyl)-1-chloro-1-methylheptane.

A solution of the above chloride in 660 ml. dichloromethane was added to a solution of 947 ml. of 25% trimethylaluminum (3.28 M) in hexane, dissolved in 1.9 l. of dichloromethane. The addition was completed over a period of 1.5 hours while the reaction temperature was maintained at −18° to −20° C. The reaction was stirred 1 hour longer at −15° C. and overnight at −3° C. The reaction was then quenched by slow addition to 2 l. of ice with simultaneous slow addition of 540 ml. of concentrated hydrochloric acid. The organic layer was separated and the aqueous layer extracted with 500 ml. dichloromethane. The combined organic extract was washed with 500 ml. saturated sodium bicarbonate, dried over magnesium sulfate and evaporated to an oil. The crude product was distilled to yield 525 g. (80%) of the title compound as an oil.

BP 168°–176° C. (0.3 torr).

IR (CHCl$_3$) 1604 and 1581 cm$^{-1}$.

HRMS (m/e) 310.2351 (M+, Calcd. for C$_{22}$H$_{30}$O: 310.2289). 225.1304 (M+ −C$_6$H$_{13}$, Calcd. for C$_{16}$H$_{17}$O: 225.1275).

PMR (CDCl$_3$) $\delta$0.82 (m, CH$_3$), 1.17 (m, CH$_2$), 1.23 (s, CH$_3$), 1.5 (m, CH$_2$), 5.00 (s, CH$_2$) and 6.6–7.5 (m, PhH).

EXAMPLE 4

2-Benzyloxy-1-bromo-4-(1,1-dimethylheptyl)benzene

To a −78° C. solution of 42.6 g. (0.134 mole) of 1-benzyloxy-3-(1,1-dimethylheptyl)benzene and 12.2 g. (0.200 mole) of t-butylamine in 300 ml. of dichloromethane was added a solution of 27.2 g. (0.151 mole), bromine in 100 ml. of dichloromethane. The reaction mixture was then allowed to warm to 25° C. and added to 500 ml. saturated sodium sulfite and 500 ml. ether. The organic extract was washed with two 500 ml. portions of saturated sodium bicarbonate, dried over magnesium sulfate and evaporated to an oil. The crude product was purified via column chromatography on 500 g. of silica gel eluted with 10% ether-hexane to give 41.9 g. (80%) of the title compound as an oil.

IR (CHCl$_3$) 1587, 1570 and 1481 cm$^{-1}$.

MS (m/e) 390, 388 (M+), 309, 299 and 91.

PMR (CDCl$_3$) δ0.80 (m, terminal methyl), 1.20 (s, gem dimethyl), 5.05 (s, benzylic methylene), 6.8 (m, ArH) and 7.35 (m, ArH and PhH).

PREPARATION A

4-[2-Benzyloxy-4-(1,1-dimethylheptyl)phenyl]-2-butanone

A solution of 3.89 g. (0.010 mol.) of 1-bromo-2-benzyloxy-4-(1,1-dimethylheptyl)benzene in 15 ml. of tetrahydrofuran was slowly added to 0.36 g. (0.015 mol.) of 70-80 mesh magnesium metal. The resultant mixture was refluxed for 20 minutes and was then cooled to −10° C. Cuprous iodide (0.115 g., 0.006 mol.) was added and stirring continued for 10 minutes. To the resultant mixture was slowly added a solution of 0.701 g. (0.010 ml.) of metyl vinyl ketone in 5 ml. of tetrahydrofuran at such a rate that the reaction temperature could be maintained below 0° C. The reaction mixture was stirred for 30 minutes longer (t<0° C.) and then added to 100 ml. of 1 N hydrochloric acid and 100 g. of ice. The quenched reaction was extracted three times with 150 ml. portions of ether. The combined ether extract was washed twice with 100 ml. portions of water, twice with 100 ml. portions of saturated sodium chloride, dried over magnesium sulfate and evaporated to an oil. The oil was purified via column chromatography on 180 g. of silica gel eluted with 20% ether-cyclohexane to yield 1.07 g. (28%) of the title compound as an oil.

PMR δCDCl$_3$$^{TMS}$0.80 (m, terminal sidechain methyl), 1.22 (s, gem dimethyl), 2.03 (s, CH$_3$CO), 2.72 (m, two methylenes), 5.00 (s, benzyl ether methylene), 6.6-6.8 (m, ArH), 6.90 (d, J=8 Hz, ArH) and 7.22 (bs, PhH).

PREPARATION B

4-[2-Benzyloxy-4-(1,1-dimethylheptyl)phenyl]-2-butanol

To a −15° C. solution of 0.5 g. (1.31 mmols.) of 4-[2-benzyloxy-4-(1,1-dimethylheptyl)phenyl]-2-butanone in 5 ml. of methanol was added 50 mg. (1.31 mmols.) of sodium borohydride. The reaction mixture was stirred for 30 minutes and then added to 100 ml. of saturated sodium chloride 150 ml. ether. The ether extract was washed once with 100 ml. of saturated sodium chloride, dried over magnesium sulfate and evaporated in an oil. The oil was purified via column chromatography on 100 g. of silica gel eluted with 1:1 ether:cyclohexane to yield 419 mg. (84%) of the title compound as an oil.

PMR δCDCl$_3$$^{TMS}$0.8 (m, terminal sidechain methyl), 1.10 (d, J=7 Hz, carbinol methyl), 1.23 (s, gem dimethyl), 2.6-2.9 (m, two methylenes), 3.63 (sextet, carbinol methine), 5.00 (s, benzyl ether methylene), 6.8-7.3 (m, ArH) and 7.30 (bs, PhH).

PREPARATION C

4-[4-(1,1-Dimethylheptyl)-2-hydroxyphenyl]-2-butanol

A mixture of 390 mg. (1.02 mmols.) of 4-[2-benzyloxy-4-(1,1-dimethylheptyl)phenyl]-2-butanol, 360 mg. of solid sodium bicarbonate, 100 mg. of 10% palladium-on-carbon and 10 ml. of ethanol was stirred under one atmosphere of hydrogen for 20 minutes. The reaction mixture was filtered through diatomaceous earth with ethyl acetate and evaporated to an oil. The oil was purified via rapid column chromatography on silica gel eluted with ether to give a quantitative yield of the title compound as an oil.

PMR δCDCl$_3$$^{TMS}$0.85 (m, terminal sidechain methyl), 1.25 (s, gem dimethyl), 1.62 (m, C-3 methylene), 2.6 (m, C-4 methylene), 3.9 (m, C-2 methine and two OH), 6.90 (dd, J=8 and 2 Hz, ArH), 6.86 (d, J=2 Hz, ArH) and 7.02 (d, J=8 Hz, ArH)

IR (CHCl$_3$) 3597, 3300, 1629 and 1575 cm$^{-1}$.

MS (m/e) 292 (M+), 274, 233, 207 and 189.

I claim:

1. 1-(3-Benzyloxyphenyl)-1-chloro-1-methylheptane.
2. 2-(3-Benzyloxyphenyl)-1-methylheptan-1-ol.

* * * * *

UNITED STATES PATENT AND TRADEMARK OFFICE
CERTIFICATE OF CORRECTION

PATENT NO. : 4,360,700
DATED : November 23, 1982
INVENTOR(S) : Lawrence Sherman Melvin, Jr.

It is certified that error appears in the above-identified patent and that said Letters Patent are hereby corrected as shown below:

Col. 3, line 53, "1433" should read --1443--.

Col. 6, line 44, "2-" should read -- 1- --.

Signed and Sealed this

Twenty-second Day of February 1983

[SEAL]

Attest:

*Attesting Officer*

GERALD J. MOSSINGHOFF
*Commissioner of Patents and Trademarks*